(12) United States Patent
McSwain et al.

(10) Patent No.: US 8,598,402 B2
(45) Date of Patent: Dec. 3, 2013

(54) BUTANE ABSORPTION SYSTEM FOR VENT CONTROL AND ETHYLENE PURIFICATION

(75) Inventors: C. V. McSwain, Corpus Christi, TX (US); George C. Seaman, Corpus Christi, TX (US)

(73) Assignee: Celanese International Corporation, Irving, TX (US)

( * ) Notice: Subject to any disclaimer, the term of this patent is extended or adjusted under 35 U.S.C. 154(b) by 903 days.

(21) Appl. No.: 12/223,206

(22) PCT Filed: Jan. 30, 2007

(86) PCT No.: PCT/US2007/002348
§ 371 (c)(1),
(2), (4) Date: Mar. 15, 2010

(87) PCT Pub. No.: WO2007/092187
PCT Pub. Date: Aug. 16, 2007

(65) Prior Publication Data
US 2010/0174128 A1    Jul. 8, 2010

Related U.S. Application Data

(60) Provisional application No. 60/771,124, filed on Feb. 7, 2006.

(51) Int. Cl.
*C07C 5/00* (2006.01)

(52) U.S. Cl.
USPC .......... 585/809; 585/800; 585/802; 585/818; 585/820; 585/833; 585/500

(58) Field of Classification Search
USPC ......... 585/500, 654, 655, 658, 638, 800, 802, 585/809, 818, 820, 833
See application file for complete search history.

(56) References Cited

U.S. PATENT DOCUMENTS

| | | | | |
|---|---|---|---|---|
| 4,524,236 A | | 6/1985 | McCain | 585/658 |
| 5,162,578 A | | 11/1992 | McCain, Jr. et al. | 562/512.2 |
| 5,202,521 A | * | 4/1993 | Brown et al. | 585/848 |
| 5,546,764 A | * | 8/1996 | Mehra | 62/625 |
| 5,675,054 A | * | 10/1997 | Manley et al. | 585/809 |
| 6,790,983 B1 | | 9/2004 | Zeyss et al. | 560/208 |
| 6,852,877 B1 | * | 2/2005 | Zeyss et al. | 560/241 |

FOREIGN PATENT DOCUMENTS

EP    0 407 091    1/1991

* cited by examiner

*Primary Examiner* — In Suk Bullock
*Assistant Examiner* — Sharon Pregler
(74) *Attorney, Agent, or Firm* — Michael W. Ferrell

(57) ABSTRACT

The present invention describes a n-butane absorption process for purifying the ethylene product from an ethane oxidation process. The ethane oxidation product is fed to a series of absorption towers using a n-butane solvent that remove the inert components as well as purifying the ethylene from the product. A first absorption tower uses n-butane as a solvent to absorb both the ethane and ethylene, allowing for inert gasses to be removed from the stream. An ethylene-rich side stream from this tower is sent to an ethylene purification tower where ethylene is purified using n-butane solvent. The bottom stream from the first absorption tower is then sent to an intermediate ethylene recovery tower where crude ethylene is purified, and the overhead ethylene stream being sent to the ethylene purification tower. The bottoms stream, along with the bottoms stream of the ethylene purification tower, both of which comprise mostly ethane and n-butane, are then sent to a stripper tower for ethane recovery and n-butane solvent recover.

10 Claims, 2 Drawing Sheets

BUTANE ABSORPTION SYSTEM FOR VENT CONTROL AND ETHYLENE PURIFICATION

FIELD OF THE INVENTION

The invention relates generally to an integrated process for the purification of an ethylene stream that contains ethane. Such streams are commonly found as the products of ethane oxidation reactors, where ethane is oxidized into acetic acid and ethylene.

BACKGROUND OF THE INVENTION

The oxidative dehydrogenation of ethane to acetic acid and/or ethylene in the gas phase at high temperatures is known in the art. For example, U.S. Pat. No. 4,568,790 describes a process for oxidizing ethane to ethylene using an oxide catalyst. The calculated selectivity for ethylene at 50 percent conversion of ethane ranges from 63 to 76 percent. U.S. Pat. No. 4,524,236 describes a process for oxidizing ethane to ethylene using an oxide catalyst wherein the selectivity for ethylene at 51 percent conversion of ethane is as high as 80 percent. U.S. Pat. No. 5,162,578 describes a process for the selective preparation of acetic acid from ethane, ethylene or mixtures thereof with oxygen that results in an acetic selectivity of 34 percent and an ethylene selectivity of 62 percent with an ethane conversion of 4 percent. A further process for the preparation of a product comprising ethylene and/or acetic acid is described in European Patent No. EP 0 407 091 B1. According to this process, ethane and/or ethylene and a gas containing molecular oxygen is brought into contact at elevated temperature with a mixed metal oxide catalyst, resulting in a maximum selectivity for acetic acid of 78 percent at 14.3 percent ethane conversion. The highest selectivity for ethylene was 70 percent at 15 percent ethane conversion.

Vinyl acetate is generally prepared commercially by contacting acetic acid and ethylene with molecular oxygen in the presence of a catalyst active for the production of vinyl acetate. Integrated processes for producing vinyl acetate are also known in the art. For example, U.S. Pat. No. 6,852,877, which is incorporated by reference herein in its entirety, discloses a process for the production of vinyl acetate comprising (1) reacting ethane with oxygen in the presence of a catalyst to produce acetic acid (ethane oxidation), (2) reacting ethane with oxygen in the presence of a catalyst to produce ethylene (ethane oxidative dehydrogenation); (3) reacting the ethylene and acetic acid produced above with oxygen in the presence of a catalyst to produce a vinyl acetate product stream; and (4) separating the vinyl acetate from the product stream from step (3).

Furthermore, commonly owned U.S. Pat. No. 6,790,983, which is incorporated by reference herein in its entirety, discloses a process for the production of vinyl acetate comprising (1) reacting ethane with oxygen in the presence of a catalyst to produce acetic acid and ethylene (ethane oxidation), (2) reacting the ethylene and acetic acid produced above with oxygen in the presence of a catalyst to produce a vinyl acetate product stream; and (4) separating the vinyl acetate from the product stream from step (2).

FIG. 1 shows a common prior art ethylene/acetic acid production process. In this basic system, an ethane containing stream (1) is fed along with an oxygen containing gas (2) into an ethane oxidation reactor (3). This reactor can be either a fluidized bed or fixed-bed reactor. Inside the reactor (3), ethane is oxidized into acetic acid, ethylene, and various carbon oxides ($CO_x$). The gaseous reactor effluent (4) that contains these three primary components is fed into a recycle gas scrubber (5), which produces a top stream containing ethylene, ethane, and $CO_x$, and a bottom stream (6) which contains acetic acid, water, and heavy ends by-products. The bottom stream (6) is then purified as known in the art to provide purified acetic acid for sale or for use in a downstream vinyl acetate process (not shown). The top stream (7) from the recycle gas scrubber is routed to a processing step (8) that removes the $CO_x$ from the top stream. The purified stream is then fed to an ethane/ethylene separator, a separation that is often costly and difficult to achieve. The ethane stream (10) is recycled to the oxidation reactor (3) for further conversion into acetic acid, while the purified ethylene stream (11) is sent to a downstream unit, such as a vinyl acetate unit, or stored for future sale.

A common problem in the production of acetic acid/ethylene is purifying the ethylene stream for commercial production or for feedstock to a vinyl acetate plant. When ethane and/or ethylene is oxidized to produce acetic acid and/or ethylene, the product stream contains both ethane and ethylene. The separation of these two components is very challenging. It would therefore be desirable to develop a process where ethylene can be easily separated from ethane so as to produce ethylene for sale or for use in a downstream process, such as a vinyl acetate plant.

SUMMARY OF THE INVENTION

The present invention describes a n-butane absorption process for purifying the ethylene product from an ethane oxidation process. The ethane oxidation product is fed to a series of absorption towers that remove the inert components as well as purifying the ethylene from the product. A first absorption tower uses n-butane as a solvent to absorb both the ethane and ethylene, allowing for inert gasses to be removed from the stream. An ethylene-rich side stream from this tower is sent to a second tower, an ethylene purification tower, where ethylene is purified using a n-butane solvent. The bottoms from the first absorption tower is sent to a third tower, an intermediate ethylene recovery tower. In this tower, crude ethylene is purified, with the overhead stream being sent to the aforementioned ethylene purification tower for further refinement, and the bottoms stream, along with the bottoms stream of the ethylene purification tower, both of which comprise mostly ethane and n-butane, being sent to a stripper tower for ethane recovery and n-butane solvent recovery.

DETAILED DESCRIPTION OF THE INVENTION

Figure 1:
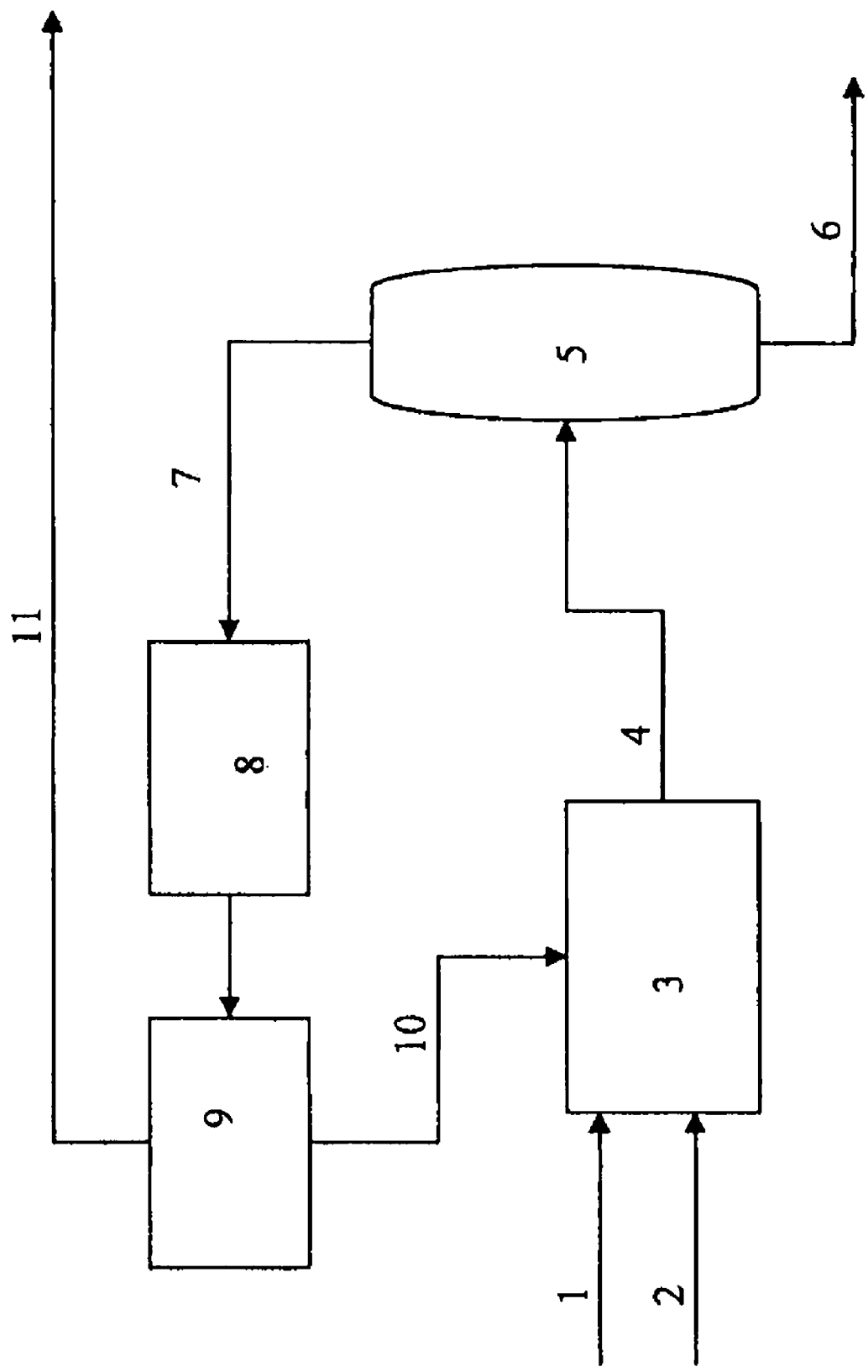
FIG. 1 shows a prior art acetic acid production process.

The present invention provides a process for separating ethylene from ethane in the product of an ethane oxidation reactor using an n-butane absorption process. The oxidation of ethane can be carried out in a fluidized bed or in a fixed bed reactor. For use in a fluidized bed, the catalyst is normally ground to a particle size in the range from 10 to 200 µm or prepared by spray drying. The gaseous feedstock, and any recycle gas combined with said feedstock gas, contains primarily ethane, but may contain some amount of ethylene, and is fed to the reactor as a pure gas or in a mixture with one or more other gases. Suitable examples of such additional or carrier gases are nitrogen, methane, carbon monoxide, carbon dioxide, air and/or steam. The gas containing molecular oxygen may be air or a gas which has a higher or lower molecular oxygen concentration than air, for example pure oxygen. The ethane oxidation reaction is generally carried out at about 400 to about 600° C., preferably about 450 to about 550° C., the key being that the temperature be high enough to oxidize ethane. The appropriate temperature will depend upon the catalyst used in the ethane oxidation reactor. There are a wide range of catalysts for use in this reaction, and one of ordinary skill in the art will know how to optimize catalyst performance by finding the appropriate reaction temperature. The pressure can be atmospheric or superatmospheric, for example about 1 to about 50 bar, preferably about 1 to about 30 bar.

The oxidation reaction produces a mixture of gases including ethylene, acetic acid, water, $CO_x$ (CO and $CO_2$), unreacted ethane, and assorted heavy by-products. This product gas normally exits the reactor at a temperature between about 450 to about 600° C. The product gas effluent from the reactor is then preferably filtered to remove catalyst fines and is then routed to a separation process, such as the recycle gas scrubber known in the art, for separating acetic acid, water, and other heavy byproducts from the ethane oxidation reactor product stream. In this a recycle gas scrubber, water, acetic acid, and other heavy byproducts are stripped from the reactor product stream and sent to a further acetic acid purification step. The overhead product comprises the unreacted ethane, ethylene, and all $CO_x$ and other inert gasses.

One of skill in the art will appreciate that the towers, scrubbers, and routing referred to in the preceding paragraphs will have associated with them various heat exchangers, pumps, and connectors and will have operating parameters that are determined by the particular mixture of gases involved. It is within the ability of one of ordinary skill in the art to determine the proper configurations and parameters, given the above disclosure. However, regardless of how the water, acetic acid, and heavies are removed from the ethane oxidation reactor product stream, it is the remaining gaseous product of unreacted ethane, ethylene, and inert gasses that is then sent to the n-butane absorption process of the present invention.

The gas stream of unreacted ethane, ethylene and inert gasses is sent to a first absorption tower for inert gas purging. This gas stream is preferably introduced in to the bottom of the absorption tower, with n-butane solvent being introduced into the top of the tower. This absorption tower operates at ethane oxidation system pressure and is used to purge inert components from the system. Operation of this tower is within the skill of one of ordinary skill in the art.

A liquid side stream from the first absorption tower rich in ethylene is removed and sent directly to a primary ethylene purification tower. In this tower, n-butane feed absorbs ethane and enhances the ethylene content of the overhead vapor stream. This purified ethylene stream can then be stored for sale, or sent to a downstream unit for further processing, such as a vinyl acetate unit. If the ethylene is sent to a vinyl acetate unit, the ethylene purification tower is preferably operated at a pressure approximating that of the vinyl acetate unit for ease of processing. The bottoms stream of this tower is sent to a stripper tower, described below, for n-butane solvent recovery. Operation of this tower is within the skill of those in the art.

The bottoms liquid stream from the first absorption tower is sent to an intermediate ethylene recovery tower. Preferably, this tower operates at a high pressure, over about 500 psia, in order to reduce the refrigeration requirements of the overhead condenser. Additional n-butane may be fed here if the separation requires, although it is not necessary. An overhead vapor stream rich in ethylene is then sent to the ethylene purification tower described above for further cutting. The bottoms stream of the intermediate ethylene recovery tower is then sent with the bottoms of the ethylene purification tower to a stripper tower and ethane tower for recovery of n-butane and ethane, respectively. Ethane from the ethane tower is recycled to the ethane oxidation process, while n-butane from the stripper tower is reused within the aforementioned absorption system.

Figure 2:
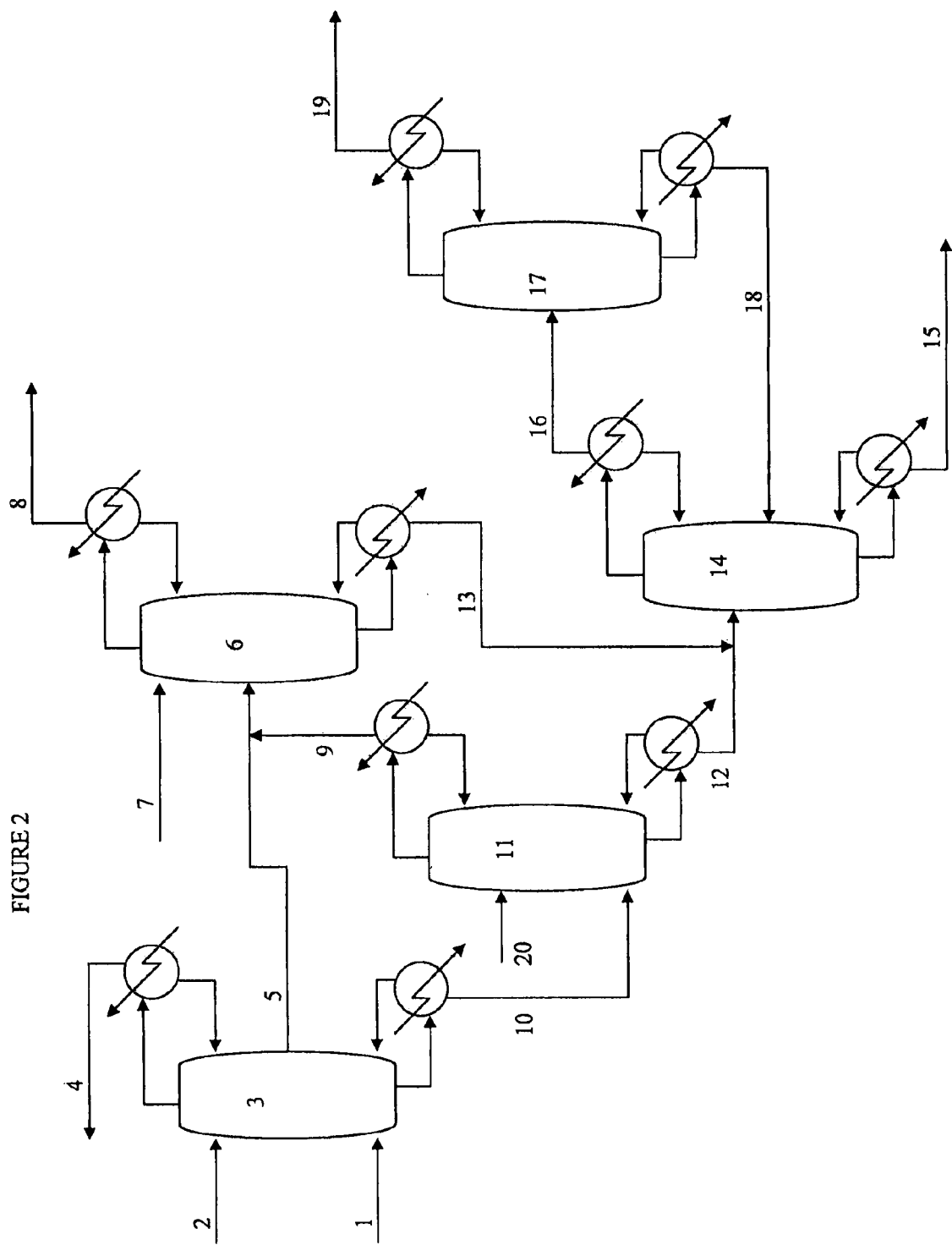
FIG. 2 shows one embodiment of the ethylene purification process of the present invention.

FIG. 2 provides a graphical description of one embodiment of this process. The gas stream (1) of unreacted ethane, ethylene and inert gasses is sent to first absorption tower (3) for inert gas purging. N-butane solvent (2) is introduced into the top of the tower for absorption of the ethane and ethylene. Uncondensed inert gasses are removed as overhead stream (4), while bottoms stream (10) is sent to intermediate ethylene recovery tower (11). An ethylene rich liquid side stream (5) from the first absorption tower (3) is sent directly to a primary ethylene purification tower (6) for ethylene purification. In this ethylene purification tower (6), n-butane feed (7) absorbs ethane and enhances the ethylene content of the ethylene overhead vapor stream (8). The bottoms stream (13) of ethylene purification tower (6) is sent to a stripper tower (14), described below, for n-butane solvent recovery.

The bottoms liquid stream from the first absorption tower (3) is sent to an intermediate ethylene recovery tower (11). Additional n-butane (20) may also be fed into this tower if the separation requires. An ethylene rich overhead vapor stream (9) is then sent to the ethylene purification tower (6) described above for further purification. The bottoms stream (12) of the intermediate ethylene recovery tower (11) is then sent with the bottoms stream (13) of the ethylene purification tower (6) to a stripper tower (14) for recovery of n-butane (15) in the bottoms stream. The overhead crude ethane stream (16) is fed to ethane tower (17) where an overhead ethane stream (19) is recovered, preferably for recycle to the ethane oxidation process. The bottoms of the ethane tower (17) is sent back to the stripper tower (14) for n-butane recovery for reuse within the aforementioned absorption system.

All of the compositions and methods disclosed and claimed herein can be made and executed without undue experimentation in light of the present disclosure. While the compositions and methods of this invention have been disclosed in terms of preferred embodiments, it will be apparent to those of skill in the art that variations may be applied to the compositions and/or methods and/or in the steps and/or in the sequence of the steps of the methods described herein without departing from the concept and scope of the invention. All such similar substitutes and modifications apparent to those of ordinary skill in the art are deemed to be within the scope and concept of the invention.

The invention claimed is:

1. A process for the production of ethylene comprising:
   (a) oxidizing ethane to produce a feed stream comprising ethylene, inert gases and ethane;
   (b) providing the feed stream to a first absorption tower wherein insert gasses are purged and ethane and ethylene are absorbed in an absorption solvent;
   (c) withdrawing an ethylene-rich sidestream from the first absorption tower and providing it to a primary ethylene purification tower;
   (d) withdrawing an absorber bottoms stream from the first absorption tower and providing it to an intermediate ethylene recovery tower;
   (e) withdrawing an overhead stream from the intermediate ethylene recovery tower and feeding it to the primary ethylene purification tower; and (f) recovering an overhead ethylene vapor stream from the primary ethylene purification tower.

2. The process of claim 1, wherein the absorption solvent is n-butane and the intermediate ethylene recovery tower has an operating pressure of about 500 psia or greater.

3. The process of claim 1, wherein the ethane is oxidized at about 400° C. to about 600° C.

4. The process of claim 1, wherein the absorption solvent is n-butane.

5. The process of claim 1, wherein the ethylene rich sidestream from the first absorption tower is combined with the overhead stream from the intermediate ethylene recovery tower prior to feeding a combined stream so formed to the primary ethylene purification tower.

6. The process of claim 1, wherein a bottoms stream from the primary ethylene purification tower and a bottoms stream from the intermediate ethylene purification tower are provided to a common stripper tower which recovers solvent as a stripper bottoms stream and produces a crude ethane overhead stream.

7. The process of claim 1, wherein ethane is recovered from a bottoms stream of the primary ethylene purification tower and from a bottoms stream of the intermediate ethylene recovery tower.

8. The process according to claim 7, wherein recovered ethane is recycled to ethane oxidation.

9. A process for the production of ethylene and recovery of ethane comprising:
   (a) oxidizing ethane to produce a feed stream comprising ethylene, inert gases and ethane;
   (b) providing the feed stream to a first absorption tower wherein insert gasses are purged and ethane and ethylene are absorbed in an absorption solvent;
   (c) withdrawing an ethylene-rich sidestream from the first absorption tower and providing it to a primary ethylene purification tower;
   (d) withdrawing an absorber bottoms stream from the first absorption tower and providing it to an intermediate ethylene recovery tower;
   (e) withdrawing an overhead stream from the intermediate ethylene recovery tower and feeding it to the primary ethylene purification tower;
   (f) recovering an overhead ethylene vapor stream from primary ethylene purification tower;
   (g) withdrawing a bottoms stream from the primary ethylene purification tower;
   (h) withdrawing a bottoms stream from the intermediate ethylene purification tower;
   (i) feeding the bottoms stream from the primary ethylene purification tower and the intermediate ethylene purification tower to a common stripper tower;
   (j) recovering a crude ethane stream from the stripper tower; and
   (k) purifying the crude ethane stream in an ethane purification tower.

10. The method of claim 9, further comprising recycling the purified ethane to ethane oxidation.

* * * * *